United States Patent [19]

Bizot et al.

[11] Patent Number: 4,466,866
[45] Date of Patent: Aug. 21, 1984

[54] ELECTROCHEMICAL PROCESS FOR THE PREPARATION OF SULPHOXIDES OF THIOFORMAMIDE DERIVATIVES, WHICH ARE USEFUL AS MEDICAMENTS

[75] Inventors: Jean Bizot, Morangis; Dominique Deprez, Montlhery, both of France

[73] Assignee: Rhone-Poulenc Sante, Courbevoie, France

[21] Appl. No.: 504,788

[22] Filed: Jun. 16, 1983

[51] Int. Cl.³ .............................................. C25B 3/02
[52] U.S. Cl. ..................................................... 204/78
[58] Field of Search .................................. 204/78, 81

[56] References Cited

U.S. PATENT DOCUMENTS 3,418,224 12/1968 Bennett et al. .......................... 204/78
4,219,393 8/1980 Torii et al. .............................. 204/78

Primary Examiner—R. L. Andrews
Attorney, Agent, or Firm—Stevens, Davis, Miller & Mosher

[57] ABSTRACT

Sulphoxides of thioformamide derivatives of the formula:

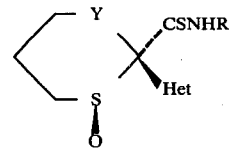

wherein R represents hydrogen or a $C_1$–$C_4$ alkyl radical, Het represents a heterocyclic radical selected from pyridin-3-yl (optionally substituted by a $C_1$–$C_4$ alkyl radical or by a halogen atom), quinolin-3-yl, pyridazin-4-yl, pyrimidin-5-yl, thiazol-5-yl, thieno[2,3-b]pyridin-5-yl and thieno[3,2-b]pyridin-6-yl, and Y represents a valency bond or a methylene radical, are prepared by oxidizing the ring sulphur atom of a thioformamide derivative of the general formula:

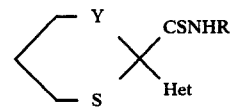

by an electrochemical method. The reaction is carried out in an electrolyte with a considerable water content, at a pH of between 7 and 7.5 and in the presence of a specific oxidizing agent $X^+$ obtained in situ from a halide $X^-$ by an electrochemical method, and at an imposed electrode potential similar to the oxidation potential of $X^-$.

The sulphoxide products are useful as medicaments for treating hypertension.

9 Claims, No Drawings

ELECTROCHEMICAL PROCESS FOR THE PREPARATION OF SULPHOXIDES OF THIOFORMAMIDE DERIVATIVES, WHICH ARE USEFUL AS MEDICAMENTS

The present invention relates to a process for the preparation of sulphoxides of thioformamide derivatives of the general formula:

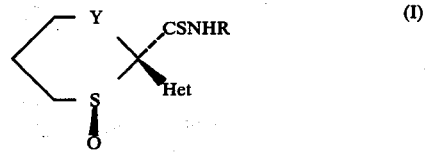

wherein R represents a hydrogen atom or a straight- or branched-chain alkyl radical containing 1 to 4 carbon atoms, Het represents a heterocyclic radical of aromatic character containing one or two nitrogen atoms selected from pyridin-3-yl (optionally substituted by a straight- or branched-chain alkyl radical containing 1 to 4 carbon atoms or by a halogen atom), quinolin-3-yl, pyridazin-4-yl, pyrimidin-5-yl, thiazol-5-yl, thieno[2,3-b]pyridin-5-yl and thieno[3,2-b]pyridin-6-yl, and Y represents a valency bond or a methylene radical.

The presence of an oxygen atom on the ring sulphur atom creates an asymmetry in the molecule which, in association with the adjacent asymmetric carbon atom, theoretically leads to 4 possible stereoisomers which, optionally, can be separated into two racemic pairs. The present invention relates to a selective process for the preparation of the sulphoxide products of general formula (I), i.e. the products in which the sulphoxide is in the trans position relative to the thioamide group.

According to the invention, the sulphoxides of general formula (I) are obtained by electrochemical oxidation of the ring sulphur atom of a thioformamide derivative of the general formula:

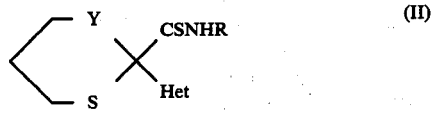

(wherein Het, R and Y are as hereinbefore defined), the reaction being carried out in an electrolyte with a considerable water content, at a pH of between 7 and 7.5 and in the presence of a specific oxidising agent $X^+$ obtained in situ from a halide $X^-$ by an electrochemical method, and at an imposed electrode potential similar to the oxidation potential of $X^-$.

In practice, to produce the oxidising agent $X^+$, it is particularly advantageous to use an alkali metal iodide such as potassium iodide, or an ammonium halide such as ammonium iodide, triethyl-n-propylammonium iodide or tetraethylammonium bromide, or otherwise an aryl iodide such as phenyl iodide, the reaction being carried out at an imposed electrode potential similar to the oxidation potential of the iodide (0.6 to 0.8 V relative to a saturated calomel reference electrode).

The electrolyte in which the reaction is carried out generally consists of:
an organic solvent miscible with water capable of dissolving the substance of general formula (II) to be oxidised, such as acetonitrile or an alcohol, e.g. methanol or ethanol,
distilled or deionised water, and
an aqueous buffer solution at pH 7, generally consisting of a mixture of 0.1M aqueous solutions of ammonium hydrogenphosphate and ammonium dihydrogenphosphate.

The relative proportions of water and organic solvent depend on the solubility in water of the sulphide of general formula (II) to be oxidised. The total percentage of water in the electrolyte can vary between 10 and 99; it is generally between 40% and 80%.

The quantity of electricity required in practice to oxidise a sulphide of general formula (II) to a sulphoxide of general formula (I) is 4 to 8 Faradays per mol.

Preferably, the oxidation is carried out in a diaphragm electrolyser at a temperature between 0° C. and the reflux temperature of the reaction mixture, preferably at between 20° and 60° C.

In a preferred embodiment of the process, the electrolytic oxidation is carried out in an electrolyser comprising an anode and a reference electrode, an anode compartment, a separating diaphragm, a cathode compartment and a cathode, the characteristics of which are as follows:

(a) The anode is a solid which cannot be attacked at the potential at which the reaction is carried out, and consists of an electrically conducting material, preferably platinum, on which the oxidation of the sulphide of general formula (II) takes place at a potential below the oxidation potential of the constituents of the solvent; this potential is measured relative to a saturated calomel reference electrode separated from the electrolyte by an agar-agar gel with KCl.

(b) The anode compartment contains the electrolyte indicated above and the sulphide of general formula (II) to be oxidised.

(c) The separating diaphragm consists of a porous material such as a plate, a sleeve or a filter candle made of sintered glass or porcelain, or alternatively consists of an ion exchange membrane, preferably a cation exchange membrane. It is particularly advantageous to use a NAFION 125 membrane (Dupont registered trademark).

(d) The cathode compartment contains the same electrolyte as the anode compartment.

(e) The cathode consists of an electrically conducting material, the nature of which is not essential to the operation of the process, and which can therefore be identical to or different from the anode material.

In a preferred embodiment of the invention, the anode, the cathode and the separating diaphragm are arranged in vertical parallel planes. Moreover, several individual electrolysers can be combined like filter presses.

A pump can be used to circulate the anolyte in closed circuit. The circuit can also comprise additional devices such as heat exchangers or expansion vessels; an expansion vessel of this type makes it possible, in particular, to feed the anolyte with sulphide of general formula (II) and also makes it possible to effect a withdrawal in order to extract the sulphoxide of general formula (I).

The catholyte can also be circulated. In a preferred embodiment of the invention, the catholyte circuit is similar to the anolyte circuit, which makes it possible to equilibrate the pressures on either side of the separating diaphragm.

In another particular embodiment of the invention, spacers are arranged in the anode and cathode compartments. The purpose of these spacers is, on the one hand, to prevent the ion exchange membrane from deforming and, on the other hand, to prevent this membrane from coming into contact with the electrodes. They are also used to improve the homogeneity of the anolyte concentration. They also create turbulences which assist the electrolysis. These spacers are generally manufactured from chemically inert and electrically non-conducting synthetic polymers. They can be made in the form of interlaced, intersecting, knotted or welded filaments (woven fabrics, grids, nets) or alternatively in the form of plates possessing holes or grooves. In practice, these spacers are orientated in planes parallel to those of the electrodes and of the diaphragm.

In another embodiment of the invention, the cell can consist simply of a parallelepipedal or cylindrical vessel made of a material which is inert towards the constituents of the electrolytes. This vessel contains the working electrode, the nature of which is the same as that defined above. The shape of this working electrode is made to suit the shape of the vessel.

In general, any electrolytic cell comprising an anode and a cathode separated by one or more diaphragms ensuring the ionic conductivity can be employed, the arrangement of the elements not being essential to the operation of the process.

The products obtained by the process according to the invention can be purified by the usual physicochemical methods, in particular crystallisation and chromatography.

The sulphides of general formula (II) can be prepared by using or adapting the methods described in the European Patent Application published under No. 0046,417.

Indirect electrochemical oxidation using an iodonium ion I$^+$ is known from the publication by TATSUYA SHONO et al. [Tetrahedron Letters, (1979), 165–168]. However, there is nothing in this publication to suggest that the process could be used to oxidise sulphides of general formula (II), and even less to oxidise them selectively.

The sulphoxides of general formula (I) obtained by the process according to the invention possess antihypertensive properties making them useful as medicaments for treating hypertension.

At doses of between 0.02 and 50 mg/kg animal body weight, administered orally, they lower the arterial pressure in spontaneously hypertensive rats (SHR) of the OKAMOTO-AOKI strain. The use of spontaneously hypertensive rats for studying antihypertensive products is described by J. L. ROBA, Lab. Anim. Sci., 26, 305 (1976).

Their lethal dose (LD$_{50}$) in mice is generally more than 300 mg/kg animal body weight administered orally.

The following non-limitative Examples illustrate the invention.

EXAMPLE 1

N-Methyl-2-(pyridin-3-yl)tetrahydrothiophen-2-carbothioamide (2 g), acetonitrile (67.5 cc), deionised water (7.5 cc), aqueous ammonium phosphate buffer [0.1M in respect of NH$_4$H$_2$PO$_4$; 0.1M in respect of (NH$_4$)$_2$HPO$_4$] at pH 7 (75 cc) and triethyl-n-propylammonium iodide (0.4 g) are introduced successively into an electrolysis cell of 150 cc capacity, comprising a working electrode consisting of a platinum grid with a surface area of 16 cm$^2$, a counter-electrode consisting of a platinum grid with a surface area of 4.5 cm$^2$, and a saturated calomel reference electrode separated from the electrolyte by an agar-agar gel with KCl. The reaction mixture, stirred by means of a polytetrafluoroethylene-coated magnetic bar, is deoxygenated by bubbling therethrough a stream of nitrogen. The potential of the working electrode is set at +0.8 V relative to the saturated calomel electrode (this is denoted as +0.8 V/SCE). After the passage of 1150 Coulombs, the solution warms up by the Joule effect and reaches a temperature of 42° C. The potential of the working electrode is then reduced to +0.65 V/SCE so as to maintain a temperature of about 45° C. The current passing through the cell is between 400 and 500 mA. During the electrolysis, an approximately 5N aqueous ammonia solution is added in order to keep the pH value close to or greater than 7. The electrolysis is stopped when the quantity of electricity which has passed through the cell is equal to 3188 Coulombs, i.e. 3.93 Faradays per mol of sulphide to be oxidised.

The reaction mixture is then concentrated to dryness under reduced pressure (20 mm Hg; 2.7 kPa). The residue is extracted twice with diethyl ether (140 cc in total); the ether phases are washed with distilled water (50 cc) and discarded. The aqueous phases are combined and extracted with ethyl acetate (20×50 cc). The organic extracts are combined and dried over sodium sulphate. The solution is filtered and the filtrate is evaporated to dryness under reduced pressure (20 mm Hg; 2.7 kPa) at 40° C. This gives a first batch of the trans form of N-methyl-2-(pyridin-3-yl)tetrahydrothiophen-2-carbothioamide 1-oxide (1394 mg) in the form of a white product melting at 207° C. after recrystallisation from ethyl acetate. [Rf=0.24; chromatography on a thin layer of silica gel; solvent: ethyl acetate/methanol (75/25 by volume)].

The aqueous layer originating from the above extraction with ethyl acetate is taken up and extracted 3 times with butanol (180 cc in total). The organic phases are combined, dried over sodium sulphate and filtered and the filtrate is concentrated to dryness under reduced pressure (20 mm Hg; 2.7 kPa) at 40° C. This gives a crude product (450 mg) which is purified by preparative chromatography on a thin layer of silica gel (eluent: ethyl acetate/methanol, 70/30 by volume). After scratching the zone containing the product (identified by UV), the product is desorbed with a mixture of ethyl acetate and methanol (50/50 by volume). This gives a second batch of the trans form of N-methyl-2-(pyridin-3-yl)tetrahydrothiophen-2-carbothioamide 1-oxide (155 mg) melting at 207° C.

The N-methyl-2-(pyridin-3-yl)tetrahydrothiophen-2-carbothioamide can be prepared as described in the European Patent Application published under No. 0046,417.

EXAMPLE 2

N-Methyl-2-(pyridin-3-yl)tetrahydrothiopyran-2-carbothioamide (2 g), acetonitrile (67.5 cc), deionised water (7.5 cc), aqueous ammonium phosphate buffer [0.1M in respect of (NH$_4$)$_2$HPO$_4$; 0.1M in respect of NH$_4$H$_2$PO$_4$] at pH 7 (75 cc) and ammonium iodide (0.25 g) are introduced successively into an electrolysis cell of 150 cc capacity, comprising a working electrode consisting of a platinum grid with a surface area of 16 cm$^2$, a counter-electrode consisting of a platinum grid with a surface area of 8 cm$^2$, and a saturated calomel reference electrode separated from the electrolyte by an agar-agar gel with KCl.

The reaction mixture, stirred by means of a polytetrafluoroethylene-coated magnetic bar, is deoxygenated by bubbling therethrough a stream of nitrogen. The potential of the working electrode is set at 300.8 V relative to the saturated calomel electrode (this will be denoted as +0.8 V/SCE). The current passing through the cell decreases from 700 mA to 150 mA.

During the electrolysis, an approximately 5N aqueous ammonia solution is added so as to keep the pH at a value close to or greater than 7. The electrolysis is stopped when the quantity of electricity which has passed through the cell is equal to 5484 Coulombs, i.e. 7.15 Faradays per mol of sulphide to be oxidised.

The reaction mixture is then concentrated to dryness under reduced pressure (20 mm Hg; 2.7 kPa). The residue is extracted 3 times with diethyl ether (50 cc in total); the ether phases are washed with distilled water (2×30 cc) and discarded. The aqueous phases are combined and extracted 10 times with ethyl acetate (300 cc in total) in order to remove the non-polar by-products. The organic phases are washed with distilled water (5×50 cc).

The aqueous phases are combined and extracted 3 times with butan-1-ol (150 cc in total). The organic phases are combined, dried over sodium sulphate and filtered and the filtrate is concentrated to dryness under reduced pressure (20 mm Hg; 2,7 kPa) at 30° C. This gives a crude product (850 mg) which is purified by preparative chromatography on a thin layer of silica gel (eluent: ethyl acetate/methanol, 70/30 by volume). After scratching of the zone containing the product (identified by UV), the product is desorbed with a mixture of ethyl acetate and methanol (50/50 by volume). This gives the trans form of N-methyl-2-(pyridin-3-yl) tetrahydrothiopyran-2-carbothioamide 1-oxide (392 mg) melting at 228° C. [Rf=0.24; chromatography on a thin layer of silica gel; solvent: ethyl acetate/methanol (75/25 by volume)].

N-Methyl-2-(pyridin-3-yl)tetrahydrothiopyran-2-carbothioamide can be prepared as described in the European Patent Application published under No. 0046,417.

We claim:

1. A process for the preparation of sulphoxides of thioformamide derivatives of the formula:

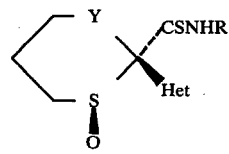

wherein R represents a hydrogen atom or a straight- or branched-chain alkyl radical containing 1 to 4 carbon atoms, Het represents a heterocyclic radical of aromatic character containing one or two nitrogen atoms selected from pyridin-3-yl (OA substituted by a straight- or branched-chain alkyl radical containing 1 to 4 carbon atoms or by a halogen atom), quinolin-3-yl, pyridazin-4-yl, pyrimidin-5-yl, thiazol-5-yl, thieno[2,3-b]-pyridin-5-yl and thieno[3,2-b]pyridin-6-yl, and Y represents a valency bond or a methylene radical, which comprises oxidising the ring sulphur atom of a thioformamide derivative of the formula:

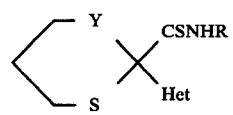

(wherein the symbols R, Het and Y are as hereinbefore defined) by an electrochemical method, the reaction being carried out in an electrolyte with a considerable water content, at a pH of between 7 and 7.5 and in the presence of a specific oxidising agent $X^+$ obtained in situ from a halide $X^-$ by an electrochemical method, and at an imposed electrode potential similar to the oxidation potential of $X^-$ and then isolating the product obtained.

2. A process according to claim 1 in which the oxidising agent $X^+$ is obtained from an ammonium halide.

3. A process according to claim 2 in which the ammonium halide is ammonium iodide.

4. A process according to claim 2 in which the ammonium halide is triethyl-n-propylammonium iodide.

5. A process according to claim 1 in which the imposed electrode potential is between 0.6 and 0.8 V relative to a saturated calomel electrode.

6. A process according to claim 1 in which the electrolyte with a considerable water content contains a water-miscible organic solvent.

7. A process according to claim 6 in which the water-miscible organic solvent is acetonitrile.

8. A process according to claim 1 in which the percentage of water in the electrolyte is between 10 and 99%.

9. A process according to claim 1 in which the percentage of water in the electrolyte is between 40 and 80%.

* * * * *